United States Patent
Frezza

(10) Patent No.: US 6,461,333 B1
(45) Date of Patent: Oct. 8, 2002

(54) SAFETY SYRINGE FOR MEDICAL USE

(75) Inventor: Pierre Frezza, Charly (FR)

(73) Assignee: Laboratoire Aquettant (FR)

( * ) Notice: Subject to any disclaimer, the term of this patent is extended or adjusted under 35 U.S.C. 154(b) by 0 days.

(21) Appl. No.: 09/530,380

(22) PCT Filed: Oct. 29, 1998

(86) PCT No.: PCT/FR98/02322
§ 371 (c)(1),
(2), (4) Date: Jul. 10, 2000

(87) PCT Pub. No.: WO99/22791
PCT Pub. Date: May 14, 1999

(30) Foreign Application Priority Data

Oct. 30, 1997 (FR) .............................. 97 13873

(51) Int. Cl.[7] .................................. A61M 5/32
(52) U.S. Cl. ...................... 604/192; 604/198
(58) Field of Search ................ 604/110, 192, 604/195, 164.01, 263, 162, 194, 196, 198

(56) References Cited

U.S. PATENT DOCUMENTS

| | | | | |
|---|---|---|---|---|
| 4,737,144 A | * | 4/1988 | Choksi | 604/198 |
| 4,915,699 A | * | 4/1990 | Kornberg | 604/195 |
| 4,929,237 A | * | 5/1990 | Medway | 604/198 |
| 4,998,924 A | * | 3/1991 | Ranford | 604/198 |
| 5,024,660 A | * | 6/1991 | McNaughton | 604/110 |
| 5,342,309 A | * | 8/1994 | Hausser | 604/110 |
| 5,573,514 A | * | 11/1996 | Stiehl et al. | 604/198 |
| 5,674,203 A | * | 10/1997 | Lewandowski | 604/197 |
| 5,713,871 A | * | 2/1998 | Stock | 604/192 |
| 6,033,387 A | * | 3/2000 | Brunel | 604/198 |
| 6,183,445 B1 | * | 2/2001 | Lund et al. | 604/198 |

FOREIGN PATENT DOCUMENTS

| | | | |
|---|---|---|---|
| FR | 2653667 | * | 5/1991 |
| WO | WO 90/13325 | * | 11/1990 |

* cited by examiner

*Primary Examiner*—Sharon Kennedy
(74) *Attorney, Agent, or Firm*—Cantor Colburn LLP

(57) ABSTRACT

This syringe comprises a tubular piece surrounding the body of the syringe and driving the stem of the plunger of the syringe. During injection, the tubular piece slides forward on the body. At the end of injection the tubular piece detaches from the stem and, its front part can continue to slide in order to sheathe the needle.

9 Claims, 3 Drawing Sheets

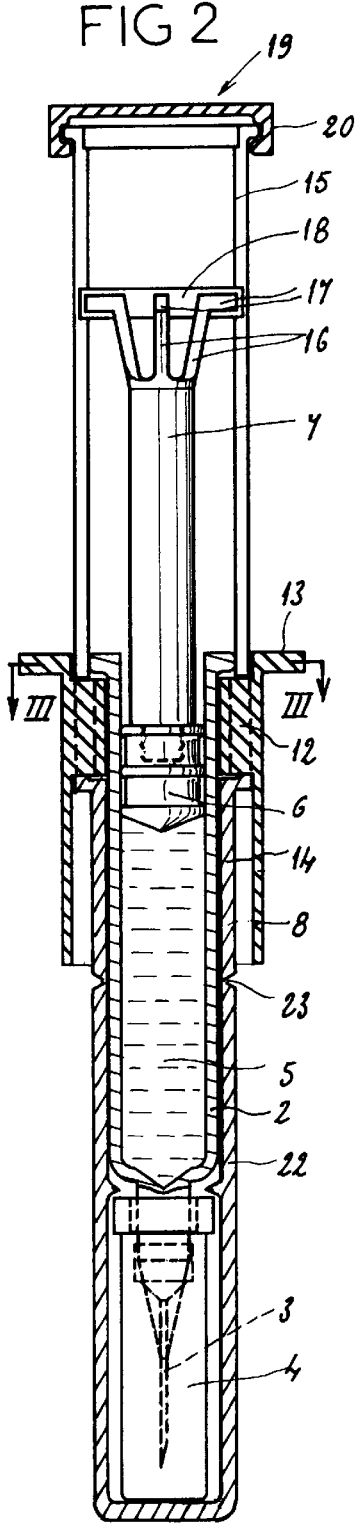
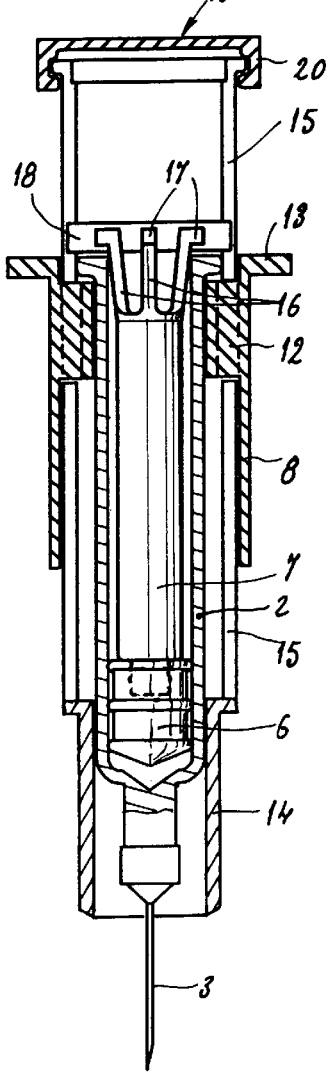
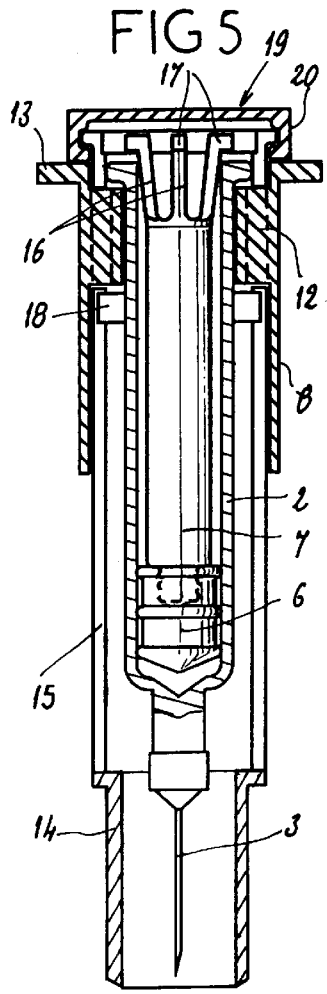

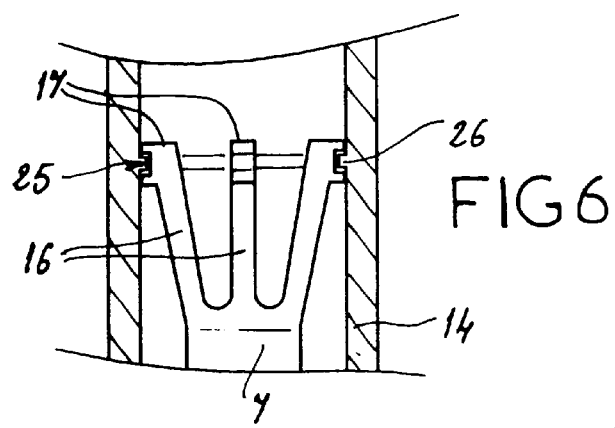
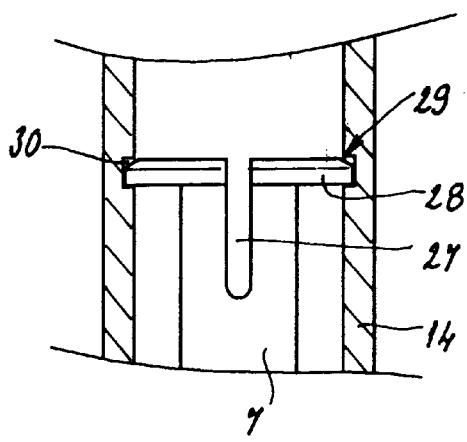
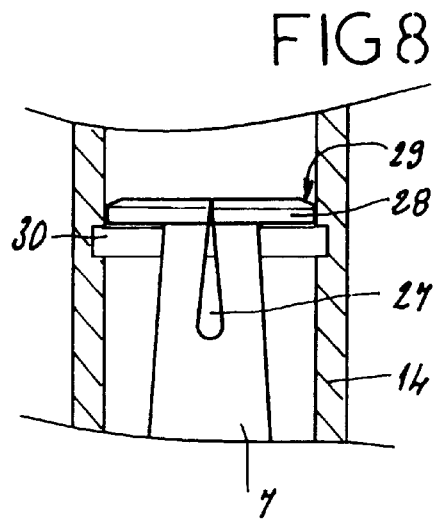
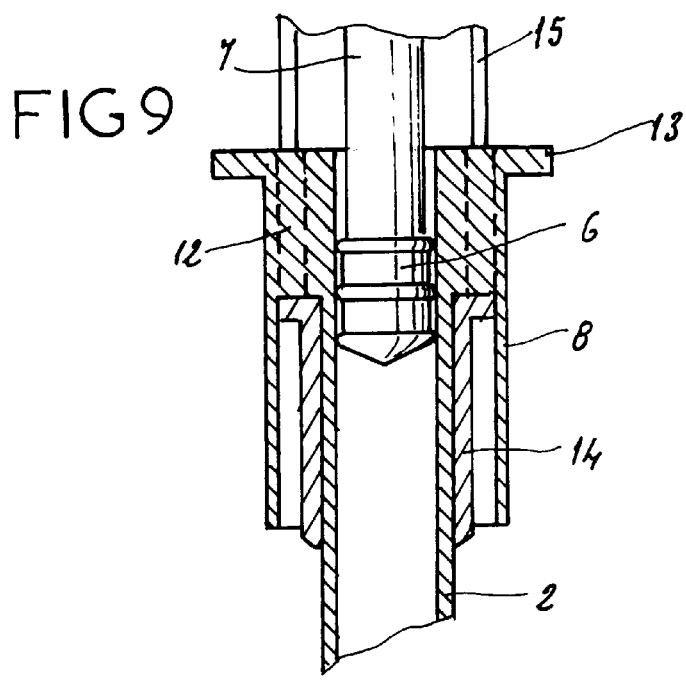

SAFETY SYRINGE FOR MEDICAL USE

TECHNICAL FIELD

The subject of the present invention is a safety syringe for medical use.

BACKGROUND OF THE INVENTION

A syringe comprises a tubular body made of glass or a synthetic substance, intended to contain the liquid that is to be injected, one end of which is equipped with an injection needle, and inside which is fitted a plunger seal that can be actuated by a stem protruding from the body at the opposite end to the end equipped with the needle. Prior to use, the needle is generally covered by a protective element, for example made of rubber. Once the liquid contained in the body of the syringe has been injected, by actuating the plunger using the stem, the needle remains bare, and this represents a risk of stick injury, which carries the risk of the transmission of certain diseases, such as hepatitis or AIDS.

As the selling price of a conventional syringe is very low, the invention aims to provide a safety syringe, the selling price of which is increased only a small amount by comparison with that of a conventional syringe, and which has a needle-protecting device which automatically covers this needle in the same movement as the injection movement so as to protect the needle after injection without the need for an additional and deliberate handling operation on the part of the user.

To this end, in the syringe to which it relates, which is of the aforementioned type, the syringe body is equipped, at its rear end, with at least one radial tab, a tubular piece of a length at least equal to the length of the syringe body increased by the length of the needle and having at least one axial slot extending from its rear end, each slot serving for the passage of one radial tab, this tubular piece being mounted so that it can slide along the body, and the stem of the plunger seal is equipped with means for axial immobilization inside the tubular piece, with this immobilization being freed at the end of the travel of the plunger seal, so as to allow the tubular piece to continue its axial movement, so that the front end of this tubular piece sheathes the needle.

Advantageously, the syringe body is equipped at its rear end with a sleeve secured to the body and coaxial therewith, to which it is connected directly or indirectly by at least one radial tab.

Prior to injection, the stem of the syringe and the tubular piece are secured one to the other. To carry out injection, the operator exerts pressure on the tubular piece. At the end of injection, the tubular piece detaches from the plunger stem and continues its forward movement, its front part then sheathing the needle, thus avoiding any risk of stick injury on this needle.

SUMMARY OF THE INVENTION

According to a first embodiment of this syringe, the means for axially immobilizing the stem of the plunger seal inside the tubular piece consist of flexible tabs secured to the end of the stem and extending the latter, these tabs facing from the inside outwards, and of which the free ends, which form a collar with a rib or a groove, collaborate respectively with a groove or annular rib formed on the inside of the tubular piece at a distance away from the rear end thereof which is at least equal to the length of the needle. At the end of injection, the tabs arranged at the rear end of the plunger stem engage in the body of the syringe, which moves the tabs closer together and allows them to detach from the tubular piece, which can thus continue its forward movement.

According to another embodiment, the means for axially immobilizing the stem of the plunger seal inside the tubular piece consist of a collar formed at the rear end of the stem of the plunger seal and projecting radially outwards, this collar being deformable by virtue of the presence of at least one axial slot open at the rear of the stem, this collar having a chamfered end edge and being intended to be engaged in an annular groove formed on the inside of the tubular piece at a distance away from the rear end thereof which is at least equal to the length of the needle.

In this case, at the end of the forward travel of the plunger, the stem is immobilized, and continued pressure exerted on the tubular piece allows the latter to detach from the rear end of the stem, given the flexibility afforded by the structure thereof.

Advantageously, the rear end of the tubular piece is closed by a cap which makes it more rigid.

The additional rigidity thus afforded is important, particularly in preventing undesired detachment between the rear end of the stem and the tubular piece.

To make the syringe easier to handle, the sleeve comprises, near its rear end, a complete or partial collar which projects outwards.

According to one possibility, the sleeve forms an integral part of the body of the syringe and is obtained by moulding a synthetic material at the same time as this body.

According to another possibility, the sleeve, produced independently of the syringe body, is secured to a bush of an inside diameter matched to the outside diameter of the syringe body.

According to one embodiment of this syringe, the tubular piece comprises, at its front end, a frangible extension intended to sheathe the needle before the syringe is used.

Before the syringe is used, the frangible extension may be separated from the tubular piece, for example by a twisting movement.

The tubular piece is short enough that, before injection, the front end of the body of the syringe is visible so as, for example, to allow the clarity of the liquid to be injected to be checked.

BRIEF DESCRIPTION OF THE DRAWINGS

In any event, the invention will be clearly understood with the aid of the description which follows, with reference to the appended diagrammatic drawing which, by way of non-limiting examples, depict two embodiments of this syringe:

FIG. 2 is a view thereof in longitudinal section and to a larger scale, prior to use;

FIGS. 4 and 5 are two views thereof in longitudinal section, one at the end of injection and the other after the needle has been withdrawn from the site of injection;

FIG. 6 is a detailed view in longitudinal section of an alternative form of the attachment of the plunger stem to the tubular piece;

FIGS. 7 and 8 are two views of an alternative form of the attachment of the stem to the tubular piece, one in the attached position and the other in the uncoupled position;

FIG. 9 is a view of an alternative form of this syringe, in which the body of the syringe is made of a synthetic material as a single piece with the sleeve surrounding the body.

DETAILED DESCRIPTION OF THE PREFERRED EMBODIMENT

Figure 1:
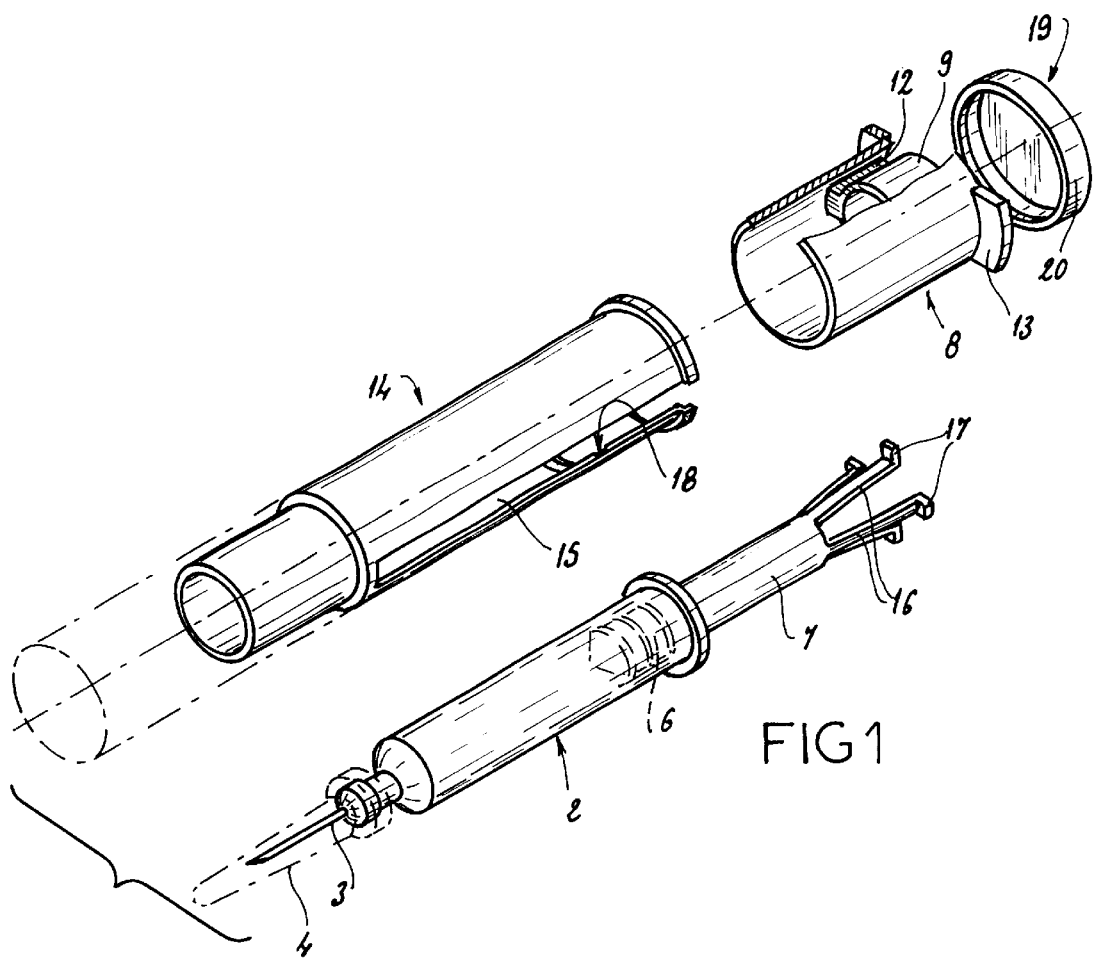
FIG. 1 is a view in exploded perspective of a first syringe.
Figure 3:
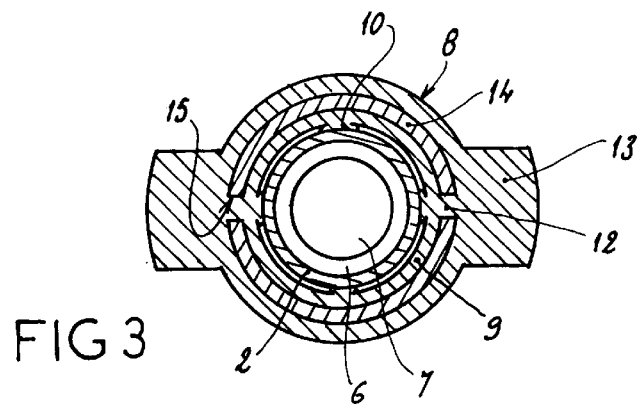
FIG. 3 is a view thereof in cross section on the line III—III of FIG. 2.

The syringe depicted in FIGS. 1 to 5 comprises a glass syringe body 2, one end of which is equipped with a separate injection needle 3 protected, prior to use, by a protector 4 depicted in chain line in FIG. 1. This syringe body 2, which is intended to contain a liquid 5 that is to be injected, is closed at its other end by a plunger seal 6, actuated by a stem 7. Mounted on the syringe body 2, in the rear part thereof, is a sleeve 8 coaxial with the syringe body and secured to the latter by a bush 9 which bears against the syringe body 2 via longitudinal ribs 10. The sleeve 8 is connected to the bush 9 by two radial tabs 12. The sleeve 8 is equipped, at its rear end, with a partial collar 13 projecting outwards.

This syringe comprises a tubular piece 14, the length of which is approximately equal to the length of the syringe body increased by the length of the needle 3 and which, starting from its rear end, has two longitudinal slots 15, each serving for the passage of one tab 12 which connects the sleeve 8 and the bush 9. The tubular piece 14 is intended to be engaged over the syringe body 2 and to slide relative to the latter inside the sleeve 8.

In the embodiment depicted in FIGS. 1 to 5, the stem 7 of the plunger 6 comprises, at its rear end, flexible tabs 16 extending the stem and facing from the inside outwards, and of which the free ends form a collar 17 facing outwards. This collar 17 is intended to be engaged in an annular groove 18 formed on the inside of the tubular piece 14, at a distance from the rear end thereof that is at least equal to the length of the needle. The rear end of the tubular piece 14 may be closed off by a cap 19 which has a rim 20 which caps the tubular piece so as to prevent the possible opening thereof which may result from the presence of the slots 15.

In the embodiment depicted in FIG. 2, the front part of the tubular piece 14 is equipped with an extension 22 which is frangible at a thinned zone 23. This extension is intended to sheathe the needle before the syringe is used. Starting out with a syringe, as depicted in FIG. 2, the use of the syringe is as follows.

The operator removes the extension 23 of the tubular piece and the needle protector 4. He may introduce the needle into the patient in an entirely normal way by holding the syringe by the sleeve 8, between the index and middle fingers, and pressing the cap 20 of the tubular piece 14 with his thumb. The axial movement of the tubular piece 14 results in a corresponding driving of the stem 7 and of the plunger 6, causing the liquid 5 contained in the syringe to be injected into the body of the patient. When, at the end of injection, the tabs 16 forming an elastic cone come into contact with the body of the syringe, the latter pushes the tabs 16 closer together and their collar 17 escapes from the groove 18 in the tubular piece 14, as shown in FIG. 4.

Throughout the injection phase, the front part of the tubular piece has gradually sheathed the syringe body 2 until, at the end of injection, it has come into contact with the skin of the patient. Continuing to push on the tubular piece 14 allows the needle to be completely sheathed by the front of the piece 14, as shown in FIG. 5, as the needle is gradually pulled out of the skin. The complete syringe is retracted into the tubular piece 14 and can be disposed of without the risk of stick injury to the operator or to cleaning staff.

FIG. 6 depicts an alternative form of the attachment of the rear end of the stem 7 to the inside of the tubular piece 14.

In this case, the flexible tabs 16 at their free ends form a collar 17, in the exterior face of which is formed a groove 25 in which an annular rib 26 formed on the inside of the tubular piece 14 is intended to engage.

The stem 7 is detached from the tubular piece 14 under the same conditions as hereinabove.

FIGS. 7 and 8 illustrate another embodiment of the invention, in which the same elements are denoted by the same references as previously. In this instance, the stem 7 is of constant cross section and has axial slots 27 opening into its rear edge. The stem 7 also has a peripheral collar 28, interrupted by the slots 27. This collar has a chamfered outer edge 29. The collar 28 is intended to engage in an annular groove 30 in the tubular piece 14 so as to put together the stem and the tubular piece. When, at the end of injection, the stem 7 is axially immobilized, the rear part of the stem 7 can close up, by virtue of the presence of the slots 27, the chamfered surfaces 29 allowing this closing-up movement and, consequently, the stem 7 can detach axially from the tubular piece 14, the translational movement of which can be continued so as to sheathe the needle, as shown in FIG. 8.

FIG. 9 depicts an alternative form of this syringe, in which the syringe body 2 is made of synthetic material and forms a single piece with the sleeve 8 to which it is connected by tabs 12. In this instance, there is no intermediate bush 9 as there was before.

As is clear from the foregoing, the invention affords a great improvement to the existing art by providing a safety syringe equipped with an automatic device for protecting the needle at the end of injection, this protection being achieved without the operator having to perform a deliberate movement. Furthermore, the selling price of this syringe is not appreciably higher than that of a conventional syringe, insofar as the protective device consists merely of one additional component—the tubular piece—or two additional components, insofar as the sleeve does not form an integral part of the syringe body.

As goes without saying, the invention is not restricted simply to the embodiments of this syringe which have been described hereinabove by way of example; on the contrary, it encompasses all alternative forms thereof.

What is claimed is:

1. A safety syringe for medical use, comprising a tubular syringe body intended to contain a liquid to be injected, one end of which is equipped with an injection needle, and inside which is fitted a plunger seal actuated by a stem protruding from the body at the opposite end to the end which is equipped with the needle, and a tubular piece mounted slidably along the syringe body, wherein the syringe body is equipped, at its rear end, with at least one radial tab, the tubular piece has a length at least equal to a length of the syringe body increased by a length of the needle and includes at least one axial slot extending from its rear end, each slot serving for the passage of one radial tab, and the stem is equipped with means for axial immobilization inside the tubular piece at an end opposite the plunger, the immobilization being released as the plunger seal reaches its stroke end, so as to allow the tubular piece to continue its axial movement, so that the front end of the tubular piece sheathes the needle.

2. Syringe according to claim 1, wherein the syringe body is equipped at its rear end with a sleeve secured to the body and coaxial therewith, to which it is connected directly or indirectly by at least one radial tab.

3. Syringe according to claim 1, wherein the means for axially immobilizing the stem of the plunger seal inside the tubular piece consist of flexible tabs secured to the end of the stem and extending the latter, these tabs facing from the inside outwards, and of which the free ends, which form a collar with a rib or a groove, collaborate respectively with a groove or annular rib formed on the inside of the tubular piece at a distance away from the rear end thereof which is at least equal to the length of the needle.

4. Syringe according to claim 1 wherein the means for axially immobilizing the stem of the plunger seal inside the tubular piece consist of a collar formed at the rear end of the stem of the plunger seal and projecting radially outwards, this collar being deformable by virtue of the presence of at least one axial slot open at the rear of the stem, this collar having a chamfered end edge and being intended to be engaged in an annular groove formed on the inside of the tubular piece at a distance away from the rear end thereof which is at least equal to the length of the needle.

5. Syringe according to claim 1 wherein the rear end of the tubular piece is closed by a cap which makes it more rigid.

6. Syringe according to claim 2 wherein the sleeve comprises, near its rear end, a complete or partial collar which projects outwards.

7. Syringe according to claim 2 wherein the sleeve forms an integral part of the body of the syringe and is obtained by moulding a synthetic material at the same time as this body.

8. Syringe according to claim 2, wherein the sleeve, produced independently of the syringe body, is secured to a bush of an inside diameter matched to the outside diameter of the syringe body.

9. Syringe according to claim 1 wherein the tubular piece comprises, at its front end, a frangible extension intended to sheathe the needle before the syringe is used.

* * * * *

UNITED STATES PATENT AND TRADEMARK OFFICE
CERTIFICATE OF CORRECTION

PATENT NO.         : 6,461,333 B1                                            Page 1 of 1
APPLICATION NO. : 09/530380
DATED              : October 8, 2002
INVENTOR(S)        : Pierre Frezza It is certified that error appears in the above-identified patent and that said Letters Patent is hereby corrected as shown below:

On the title page (73), delete "Aquettant" and insert therefor --Aguettant--.

Signed and Sealed this

Fourth Day of September, 2007

JON W. DUDAS
*Director of the United States Patent and Trademark Office*